United States Patent
Crest et al.

(10) Patent No.: US 10,067,144 B2
(45) Date of Patent: *Sep. 4, 2018

(54) ANTIBODIES AGAINST HUMAN SODIUM CHANNEL NAV 1.9

(71) Applicants: GALDERMA RESEARCH & DEVELOPMENT, Biot (FR); CENTRE NATIONAL DE LA RECHERCHE SCIENTIFIQUE, Paris (FR); UNIVERSITE D'AIX-MARSEILLE, Marseilles (FR)

(72) Inventors: Marcel Crest, Marseilles (FR); Patrick Delmas, Vitrolles (FR); Aurélie Lonigro-Rame, Ensues la Redonne (FR); Nancy Osorio, Cavalaire sur Mer (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/757,490

(22) PCT Filed: Jun. 27, 2014

(86) PCT No.: PCT/FR2014/051641
§ 371 (c)(1),
(2) Date: May 5, 2016

(87) PCT Pub. No.: WO2014/207400
PCT Pub. Date: Dec. 31, 2014

(65) Prior Publication Data
US 2017/0131292 A1      May 11, 2017

(30) Foreign Application Priority Data
Jun. 28, 2013  (FR) .................... 13 56354

(51) Int. Cl.
*G01N 33/68* (2006.01)
*C07K 16/28* (2006.01)

(52) U.S. Cl.
CPC ......... *G01N 33/6872* (2013.01); *C07K 16/28* (2013.01); *C07K 2317/33* (2013.01); *C07K 2317/34* (2013.01); *G01N 2800/20* (2013.01); *G01N 2800/205* (2013.01)

(58) Field of Classification Search
CPC ........... G01N 33/6872; G01N 2800/20; G01N 2800/205; C07K 16/28; C07K 2317/33; C07K 2317/34
See application file for complete search history.

(56) References Cited

U.S. PATENT DOCUMENTS 8,491,893 B2 *   7/2013   Olle .................... C07K 16/30
                                                   424/130.1

FOREIGN PATENT DOCUMENTS

WO        2007/023298 A2      3/2007

OTHER PUBLICATIONS

Black Ja, et al. Annals of Neurology. 64(6):644-653. Dec. 2008. Available online at—DOI: 10.1002/ana.21527.*
Stratagene Catalog. p. 39, 1988.*
English Translation of the International Search Report dated Nov. 5, 2014 corresponding to International Patent Application No. PCT/FR2014/051641, 3 pages.
Strickland, I.T., et al., "Changes in the expression of Nav1.7. Nav1.8 and Nav1.9 in a distinct population of dorsal root ganglia innervating the rat knee joint in a model of chronic inflammatory joint pain," European Journal of Pain, vol. 12, No. 5, Jul. 2008, pp. 564-572.
Padilla, F., et al., "Expression and localization of the Nav1.9 sodium channel in enteric neurons and in trigeminal sensory endings: Implication for intestinal reflex function and orofacial pain," Molecular and Cellular Neurosciences, vol. 35, No. 1, Apr. 2007, pp. 138-152.
Lolignier, S., et al.. "Nav1.9 Channel Contributes to Mechanical and Heat Pain Hypersensitivity Induced by Subacute and Chronic Inflammation," PLOS ONE, vol. 6, No. 8, Aug. 2011, pp. 1-11.
Yu, Yao-Qing, et. al.. "Activation of Tetrodotoxin-Resistant Sodium Channel Nav1.9 in Rat Primary Sensory Neurons Contributes to Melittin-Induced Pain Behavior," Neuromolecular Medicine, vol. 15, No. 1, Mar. 2013, pp. 209-217.
Yu, F.H., et al., "Overview of the voltage-gated sodium channel family," Genome Biology, Biomed Central LTD., vol. 4, No. 3, Article 207, Jan. 20013, 8 pages.
International Search Report and Written Opinion dated Nov. 5, 2014 corresponding to International Patent Application No. PCT/FR2014/051641, 12 pages.

* cited by examiner

*Primary Examiner* — Robert S Landsman
(74) *Attorney, Agent, or Firm* — Dentons US LLP

(57) ABSTRACT

Antibodies against the human sodium channel Nav 1.9 are described. Also described, is the use of such antibodies in the diagnosis of inflammatory skin diseases. A process for preparing antibodies directed against the human Nav 1.9 is also described.

Figure 1A:
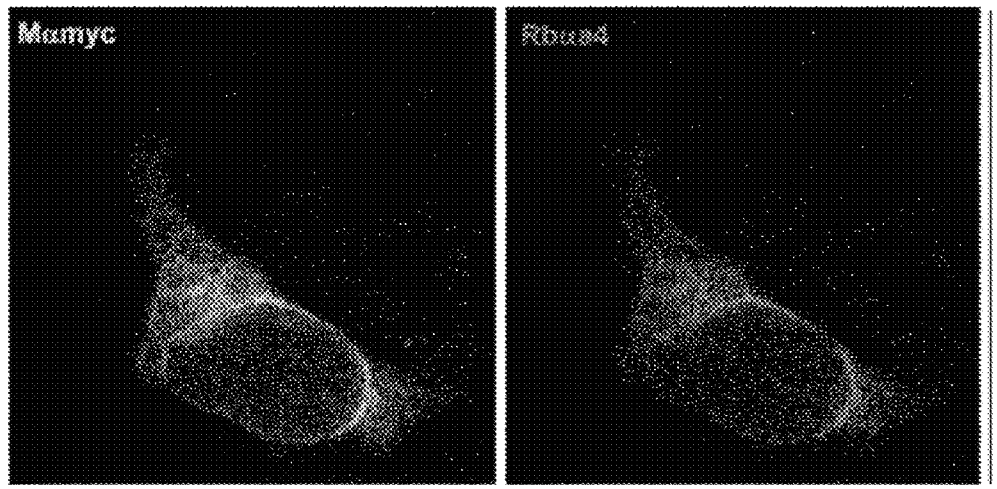

23 Claims, 8 Drawing Sheets
Specification includes a Sequence Listing.

ANTIBODIES AGAINST HUMAN SODIUM CHANNEL NAV 1.9

CROSS-REFERENCE TO PRIOR APPLICATIONS

This application is a National Stage of PCT/FR2014/051641, filed Jun. 27, 2014, and designating the United States (published on Dec. 31, 2014, as WO 2014/207400 A1), which claims priority under 35 U.S.C. § 119 to French Patent Application No. 1356354, filed Jun. 28, 2013, each hereby expressly incorporated by reference in its entirety and each assigned to the assignee hereof.

FIELD OF THE INVENTION

The invention relates to antibodies directed against the Nav 1.9 sodium channel and to their use in the diagnostic of inflammatory skin diseases, in particular rosacea.

BACKGROUND OF THE INVENTION

Inflammatory skin diseases encompass many pathologies such as rosacea, psoriasis, contact eczema, atopic dermatitis, or further pruritus.

Rosacea is a chronic and gradual common inflammatory dermatosis related to vascular disorders. It mainly affects the central portion of the face and is characterized by reddening of the face accompanied by hot flushes, facial erythema, papules, pustules, telangiectasia and sometimes ocular lesions called ocular rosacea. In extreme cases, particularly in humans, hypertrophy is observed at the nasal level called rhinophyma. Rosacea occurs between 25 and 70 years old and develops over several years with remission phases and exacerbation phases. Rosacea is much more common in persons with a pale complexion and particularly affects women. However, the most severe attacks are generally observed in men. Rosacea is classified in 4 sub-types depending on various clinical characteristics (Wilkin J et al., JAAD, 2002, 46: 584-587): erythematotelangiectatic rosacea (sub-type 1), papulopustular rosacea (sub-type 2), phymatous rosacea (sub-type 3) and ocular rosacea (sub-type 4). Rarer forms of rosacea also exist such as the granulomatous variant which is characterized by papules or yellow, brown or red indurated nodules, and by monomorphic lesions at the papules.

The pathological signs of rosacea vary according to the sub-type of the disease. Nevertheless, it is noted that local inflammatory reactions and vascular hyperactivity are constant signs of rosacea.

The pathogenesis of rosacea is poorly known and may involve several factors. The disease may be caused or promoted by the presence of follicular microorganisms such as bacteria and mites *Demodex Folliculorum*, an aberrant innate immune response, an abnormal vascular reactivity and hypersensitivity to environmental stimuli such as exposure to UVs, sudden changes in temperature, consumption of hot drinks, spiced dishes and alcohol, strong emotions (stress, embarrassment, anger . . . ).

The state of the art describes several markers useful for diagnosis of rosacea: these are for example certain interleukins (WO2013/00872), chemokine receptors or actual chemokines (WO2013/060865), the histamine receptor of type 2 (HRH-2) (FR2960152) or further a TRPV (Transient Receptor Potential Vanilloid) receptor, preferably TRPV1 (WO2012/084870).

Psoriasis is a chronic dermatosis, which evolves with eruptions or with fits, which affects about 2% of the population. Psoriasis is characterized by epidermal hyperproliferation (accelerated renewal of the epidermis) associated with keratinization disorders. Psoriasic lesions generally appear as erythemato-squamous plaques, often pruriginous plaques. Infiltration of leukocytes and moderate inflammation of the dermis and of the epidermis is generally observed at the lesions, which suggests that psoriasis would be a self-immune disease. Psoriasis frequently affects friction areas like knees, elbows and the lumbar region as well as the scalp, the hands and the feet. Several forms of psoriasis are distinguished (guttate psoriasis, pustular psoriasis, . . . ), plaque psoriasis (or vulgar psoriasis) being the most common form. Etiology of psoriasis at the present time remains poorly known. One case out of two seems to be of family origin. Various predisposition genes have been discovered (for example the allele gene HLA-Cw6). Recent studies suggest that psoriasis also results from immune anomalies (for example involvement of the (IL)-23/T-helper (Th)17 axis).

Eczema groups together pruriginous erythemato-vesicular inflammatory dermatoses. These pathologies generally develop in several phases: an erythematous phase, a vesicular phase, an exudation phase and a desquamation phase. Nummular eczema, contact eczema which is induced by an allergic reaction towards an exogenous agent, and atopic dermatitis are distinguished inter alia.

Atopic dermatitis (also called atopic dermitis or atopic eczema) is a chronic dermatosis, evolving with eruptions and which essentially affects children, in particular newly born children. Atopic dermatitis is characterized by significant skin dryness (xerosis), by papular or vesicular, squamous erythematous inflammatory lesions, with possibly cracks and lichenification of lesions. Atopic eczema affects the convexities of the cheeks, of the limbs and of the scalp in newly born children. In older children and in adults, the lesions are essentially located at the folds. Just like rosacea and psoriasis, pathogenesis of atopic dermatitis is poorly known. Genetic predisposition and/or an immune anomaly is often put forward (for example a filaggrin deficiency).

Finally, pruritus is a functional disorder which may be defined as "a sensation which causes the need to scratch oneself". It may be localized or generalized. This is a frequent symptom, in particular of inflammatory dermatoses with skin lesions such as psoriasis and atopic dermatitis. Nevertheless, certain pruritus are not associated with specific skin lesions (pruritus "sine material"). The pruritus may then be caused by a general disease, be of neurological or psychological origin or be associated with skin dryness (xerosis). The pruritus may be caused or worsened by hypersensitivity to external factors (chemicals, temperature and humidity variations, hard water . . . ). In certain cases, the pruritus is a neurological sign sustained and/or amplified by a local inflammatory reaction resulting from the scratching. There is no general marker of pruritus.

At the present time there still exists a need for new biochemical tools and new methods for diagnosing inflammatory skin diseases, in particular rosacea.

The voltage-dependent sodium channels are essential actors of the initiation and of the propagation of action potentials at so-called "excitable" cells. These sodium channels are mainly expressed at the neurones of the central and peripheral nervous system and at muscle cells. These are transmembrane proteins comprising a wide alpha ($\alpha$) sub-unit of about 260 kDa associated with one or several beta sub-units from 33 to 38 kDa. The alpha sub-unit forms the core of the channel and comprises four homologous membrane domains (I-IV), each consisting of 6 transmembrane segments (S1-S6). The membrane domains of the alpha sub-unit are connected with each other through large intracellular loops which comprise many regulation sites. The alpha sub-unit is responsible for conductance and selectivity properties of the channel while the beta sub-units are involved in the stabilization and in the kinetic properties of the channel. To this day, 10 isoforms for the alpha sub-unit have been identified in humans. The name assigned to these isoforms contains the symbol of the transported ion (Na), with as an index the regulating element (voltage v). The figures which follow, designate the sub-family of genes and the number associated with the relevant isoform. To this day, the main sub-family of genes identified comprises the isoforms Nav 1.1 to Nav 1.9. An additional isoform, further away, Nax has also been identified. The percentage of sequence identity between the different isoforms Nav 1.1 to Nav 1.9 is of at least 60%. The isoforms Nav 1.1 to Nav 1.9 inter alia differ by their sensitivity to tetrodotoxin (TTX), a very powerful and selective blocker of sodium channels, and by their tissue distribution. The isoforms Nav 1.1 to Nav 1.4, Nav 1.6 and Nav 1.7 are said to be sensitive to TTX with EC50 s of the order of one nanomolar. The isoforms Nav 1.5, Nav 1.8 and Nav 1.9 as for them are considered as resistant to TTX with EC50 s of the order of one micromolar (μM). In this respect, the EC50 of TTX for Nav 1.9 is of about 200 μM. As regards the tissue distribution, the isoforms Nav 1.1, Nav 1.2, Nav 1.3 and Nav 1.6 are mainly expressed at the central nervous system. The isoform Nav 1.4 is mainly expressed at skeletal myocytes while Nav 1.5 is essentially present, in adults, at the cardiomyocytes. Finally, the isoforms Nav 1.7, Nav 1.8 and Nav 1.9 are expressed at the peripheral nervous system (PNS). Nav 1.9 was mainly detected at the sensitive neurones of spinal ganglia by immuno-marking experiments and by PCR. Nav 1.9 would play a role in perception of pain (nociception). Finally, Nax is expressed at the heart, the uterus, smooth muscles, astrocytes and certain neurones of the hypothalamus and of the central nervous system. For a review relating to the voltage-dependent sodium channels, reference may be made to Yu and Caterall, Genome Biology, 2003, 4:207 or Caterall et al., Pharmacological Reviews, 2005, 57:397-409.

To the knowledge of the Applicants, no link was established in the state of the art between the expression of an isoform of Nav, in particular Nav 1.9, and inflammatory skin diseases.

SUMMARY OF THE INVENTION

The object of the invention is an antibody directed against human Nav 1.9 characterized in that said antibody binds to an epitope included in a peptide of sequence SEQ ID No. 1, SEQ ID No. 2 or SEQ ID No. 3. The antibody according to the invention is adapted to a use for detecting or quantifying Nav 1.9 in a biological sample, preferably a skin sample. The antibody according to the invention may be a polyclonal antibody, preferably of IgG or IgM isotype, or a monoclonal antibody. The antibody may be chimeric or humanized. It may be selected from an immunoglobulin comprising 2 heavy chains and 2 light chains, an antibody with a single domain (sdab), or an IgNar, a polypeptide comprising a variable domain of an antibody such as ScFv, VH or $V_HH$, or $V_{NAR}$, Fab, and the chimeric or humanized versions thereof.

In certain embodiments, the antibody according to the invention does not bind to Nav 1.5 and Nav 1.7, preferably human. In an additional embodiment, the antibody according to the invention is obtained from antibodies or cells expressing antibodies, from a non-human animal immunized with an antigenic compound comprising at least one peptide having at least 90% sequence identity with SEQ ID No. 1, SEQ ID No. 2 or SEQ ID No. 3. In certain embodiments, the antigenic compound comprises at least one peptide of SEQ ID No. 1, SEQ ID No. 2 or SEQ ID No. 3 or a peptide having a sequence which differs from SEQ ID No. 1, No. 2 or No. 3 because of one, two or three amino acid modifications.

The antibody according to the invention may be coupled with detection means, preferably selected from an enzyme producing a detectable signal such as horseradish peroxidase, alkaline phosphatase, β-galactosidase, or glucose-6-phosphate dehydrogenase, a chromophore, a fluorescent compound, a luminescent compound, a radionuclide such as $^{32}P$, $^{35}S$ or $^{125}I$, a metal particle, for example a gold nanoparticle, a biotin, a streptavidin, an avidin, a sugar or a lectin.

An additional object of the invention is a method for preparing an antibody directed against human Nav 1.9 comprising a step for immunizing a non-human animal with an antigenic compound comprising at least one peptide having at least 90% sequence identity with SEQ ID No. 1, SEQ ID No. 2 or SEQ ID No. 3. In certain embodiments, the antigenic compound comprises at least one peptide of SEQ ID No. 1, SEQ ID No. 2 or SEQ ID No. 3 or a peptide having a sequence which differs from SEQ ID No. 1, No. 2 or No. 3 because of one, two or three amino acid modifications. The antigenic compound may further comprise a carrier protein coupled with one or several copies of said peptide.

In certain embodiments, the preparation method according to the invention may further comprise, the recovery of the antibody directed against human Nav 1.9 from the blood plasma of the non-human animal, after immunization.

In other embodiments, the preparation method according to the invention may comprise, the production of the antibody directed against Nav 1.9 by a hybridoma obtained from a cell expressing antibodies, preferably a B lymphocyte, from the non-human animal, after immunization.

An additional object according to the invention is an antibody which may be obtained by said preparation method.

The object of the invention is also the use of an antibody according to the invention for the diagnosis, prognosis and/or prediction in vitro of an inflammatory skin disease.

An additional object is the use of an antibody according to the invention for tracking in vitro the development of an inflammatory skin disease or for evaluating in vitro the effectiveness of a drug for treating an inflammatory skin disease.

In certain embodiments, the antibody according to the invention is used for detecting or quantifying Nav 1.9 in a skin sample from a patient. In an additional embodiment, the inflammatory skin disease is selected from the group formed by rosacea, psoriasis, pruritus, contact eczema and atopic dermatitis. Preferably, this is rosacea, in particular selected from the group formed by erythematotelangiectatic rosacea (sub-type I), papulopustular rosacea (sub-type II), phymatous rosacea (sub-type III), ocular rosacea (sub-type IV) and a granulomatous variant of rosacea. In an advantageous embodiment, Nav 1.9 is detected or quantified by immunoassay, by Western blot or by immunomarking.

Finally, the object of the invention is also a kit for diagnosing an inflammatory skin disease, preferably rosacea, comprising at least one antibody according to the invention and optionally a means for detecting said antibody.

FIGURES

Figure 1B:
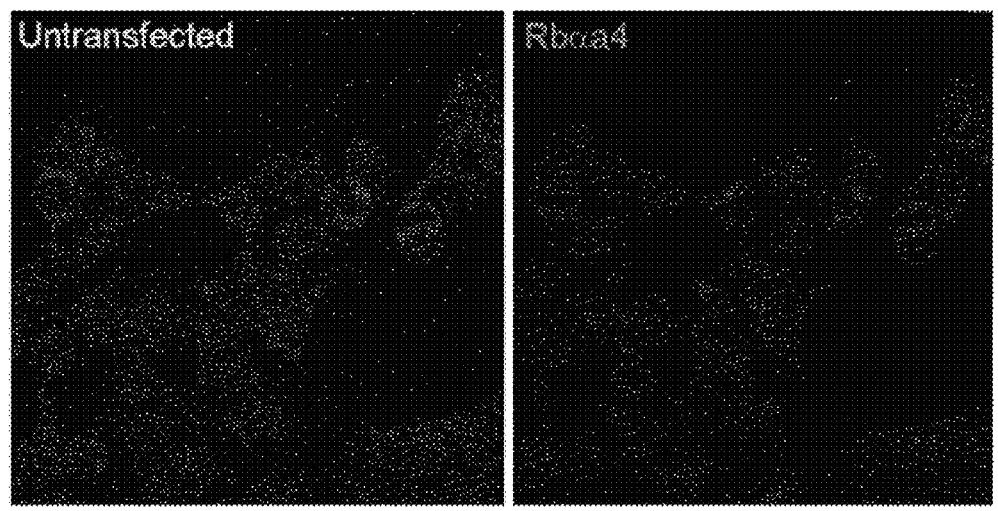

FIGS. 1A and 1B show the immunomarking results of HEK cells after fixation with 2% PAF (paraformaldehyde) by an anti-Myc monoclonal antibody and the anti-hNav 1.9 Rbαa4 antibody. FIG. 1A: cells transfected with phNav 1.9-myc. FIG. 1B: non-transfected cells.

Figure 2A:
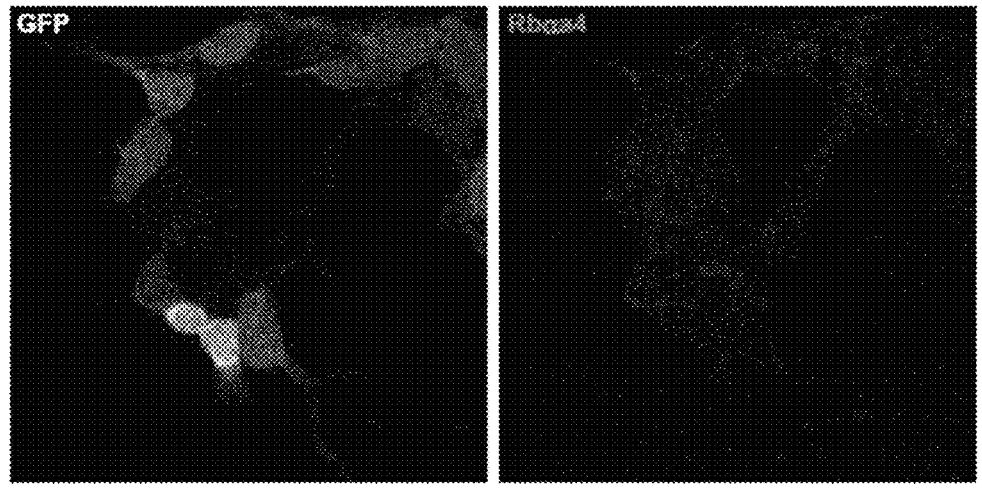
Figure 2B:
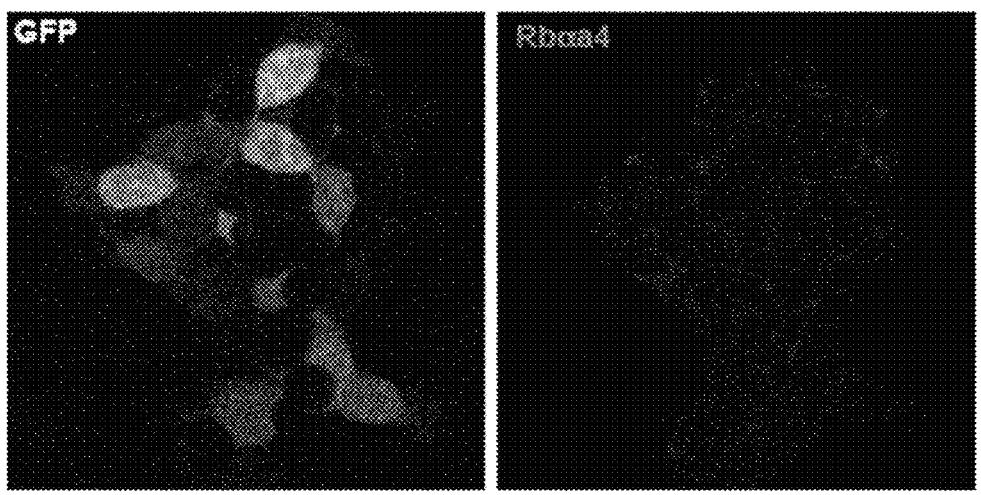

FIGS. 2A and 2B show the results of marking with the antibody Rbαa4 and of viewing with GFP for cells co-transfected by hNav 1.5 and GFP (FIG. 2A) or by hNav 1.7 with GFP (FIG. 2B). While the signal emitted by GFP is clearly visible, the marking with Rbαa4 of the cells is very weak or even inexistent.

Figure 3:
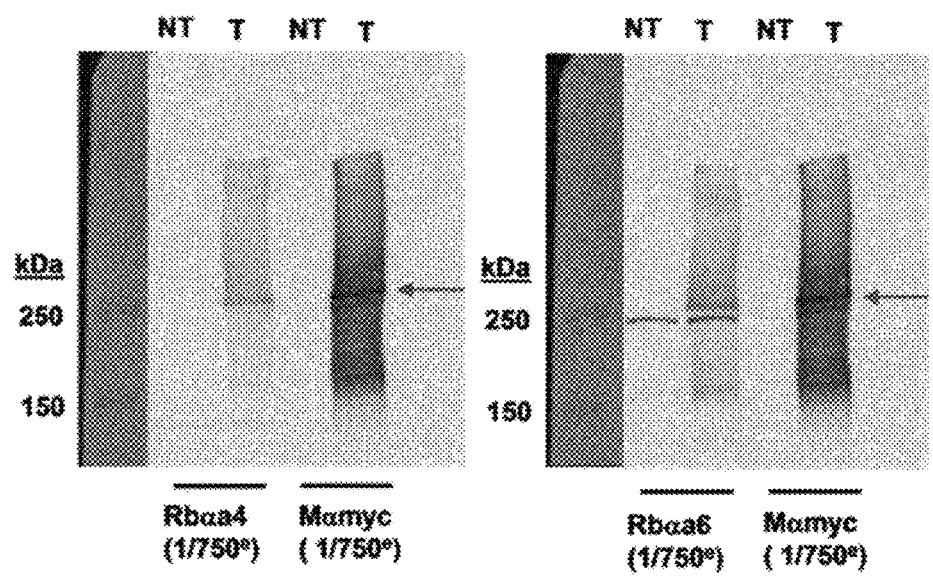

FIG. 3 shows the Western blots carried out on protein extracts of non-transfected or transfected HEK cells with a plasmid coding for hNav 1.9-myc. NT: lyzate of non-transfected cells (negative control), T: transfected cell lyzate; the antibody Rbαa6 recognizes a protein band of molecular weight 250 kDa which is not detected for non-transfected cells. Co-marking with the antibody anti-Myc is observed.

Figures 4A, 4B:
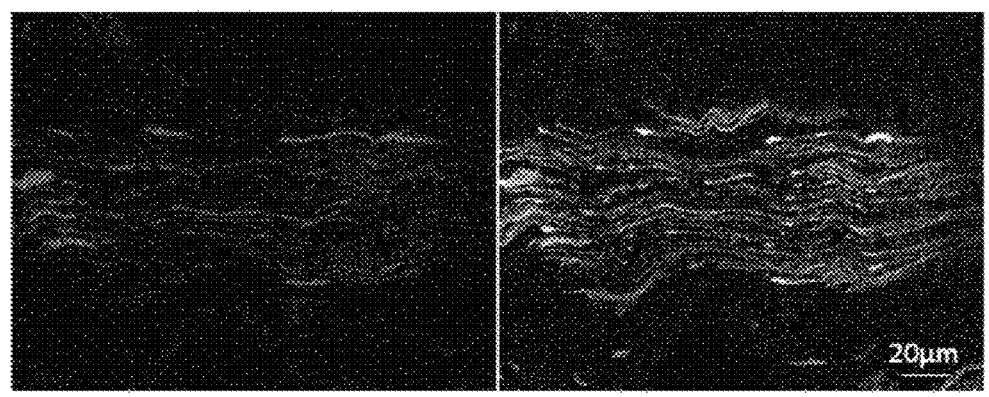

FIGS. 4A and 4B show the results of immunomarking of a deep dermis section with the antibody anti-Nav 1.9 Rbαa6 (FIG. 4A). Co-marking with an anti-peripherin antibody is illustrated in FIG. 4B. Localized expression of Nav 1.9 at the sensitive fibers of the dermis is observed.

Figures 5A, 5B, 5C:
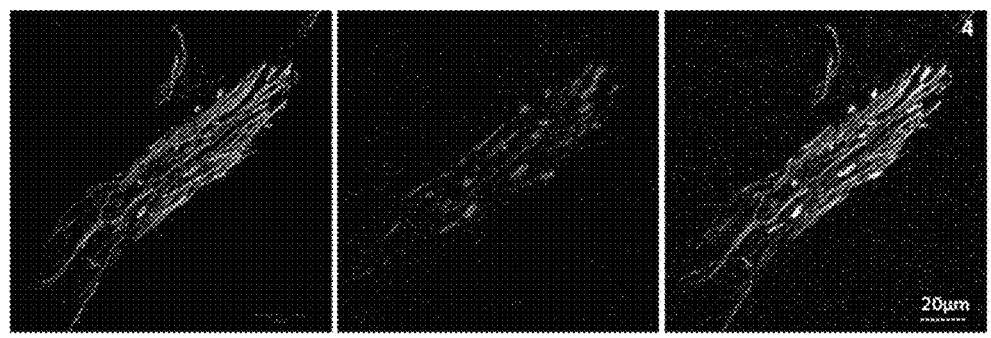

FIGS. 5A, 5B and 5C show the results of immunomarking of a deep dermis section with the anti-Nav 1.9 antibody of reference 3881.1 (FIG. 5B) and an anti-peripherin antibody (FIG. 5A). Co-marking is shown in FIG. 5C. Detection of Nav 1.9 at the sensitive fibers of the dermis is also observed.

Figures 6A, 6B, 6C:
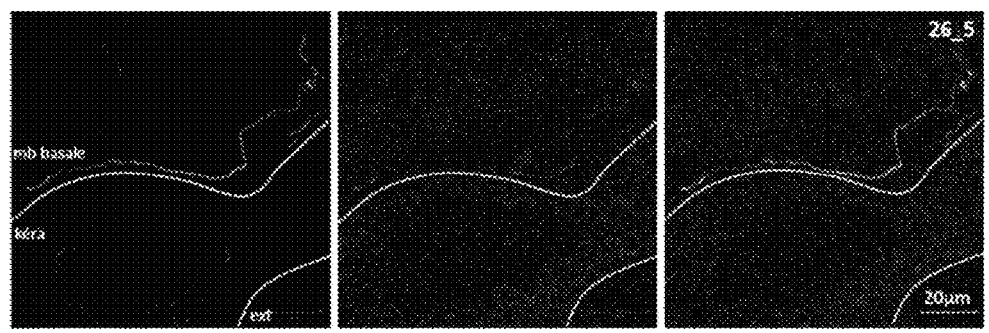

FIGS. 6A, 6B and 6C show the localized expression of Nav 1.9 at a nerve fiber isolated from the dermis, in proximity to the epidermis-dermis interface. FIG. 6A shows the marking with the anti-peripherin antibody, FIG. 6B shows the marking with the 3881 antibody. Co-marking of the peripherin and of Nav 1.9 is illustrated in FIG. 6C. Basal Mb: basal membrane, kera: keratinocyte, Ext: external.

Figures 7A, 7B, 7C:
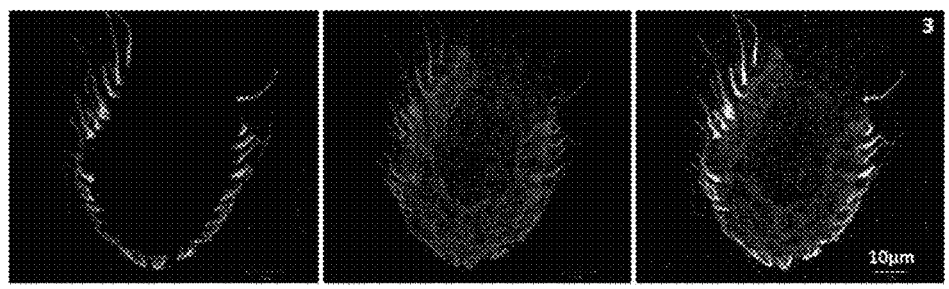

FIGS. 7A, 7B and 7C show the localized expression of Nav 1.9 at sensitive fibers innervating the hair follicle. FIG. 7A shows the marking with the anti-peripherin antibody, FIG. 7B shows the marking with the 3881 antibody. Co-marking of the peripherin and of Nav 1.9 is illustrated in FIG. 7C.

Figures 8A, 8B, 8C:
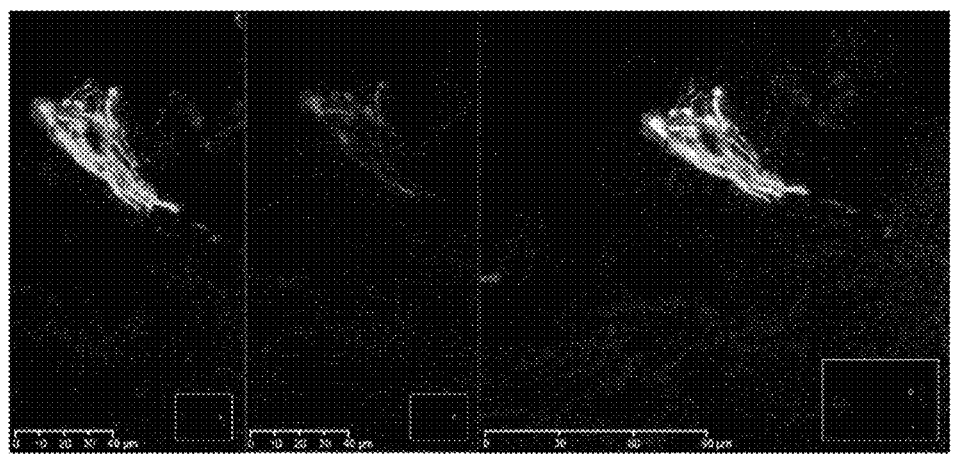

FIGS. 8A, 8B and 8C show the immunomarking of a dermis section of skin samples of patient suffering from rosacea. FIG. 8A is stained with the anti-peripherin antibody. FIG. 8B is stained with the 3881.1 antibody. Co-marking is shown in FIG. 8C.

Figures 9A, 9B, 9C:
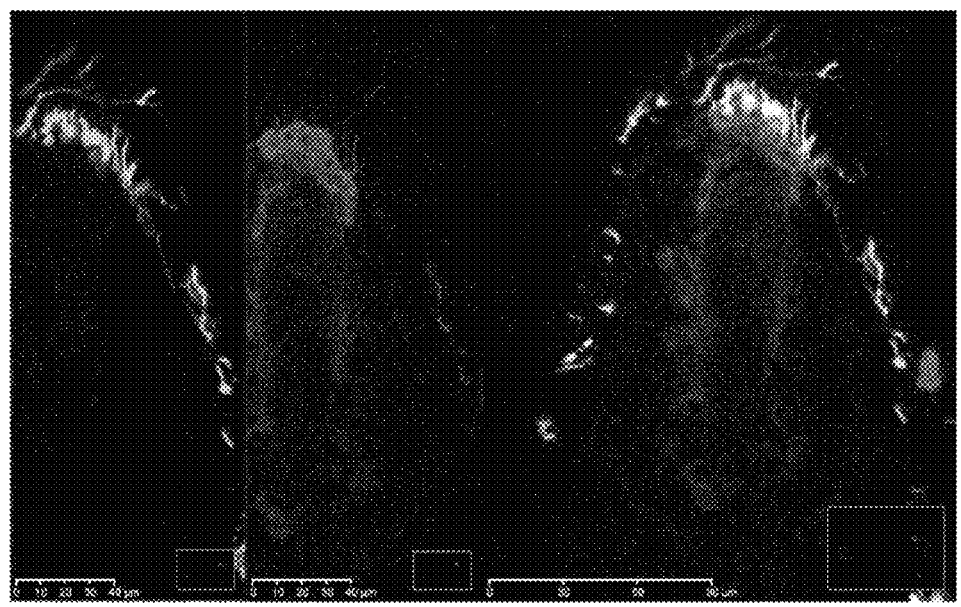

FIGS. 9A, 9B, 9C show the immunomarking of a hair follicle of skin samples of patient suffering from rosacea. FIG. 9A is stained with the anti-peripherin antibody. FIG. 9B is stained with the 3881.1 antibody. Co-marking is shown in FIG. 9C.

Figure 10A:
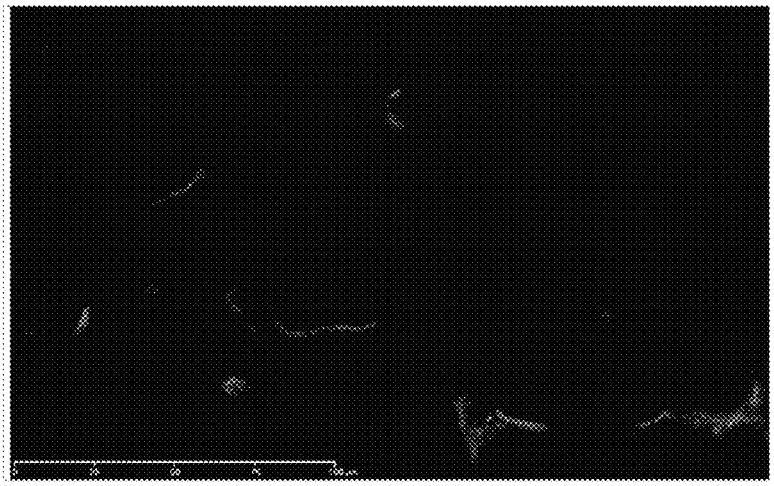
Figure 10B:
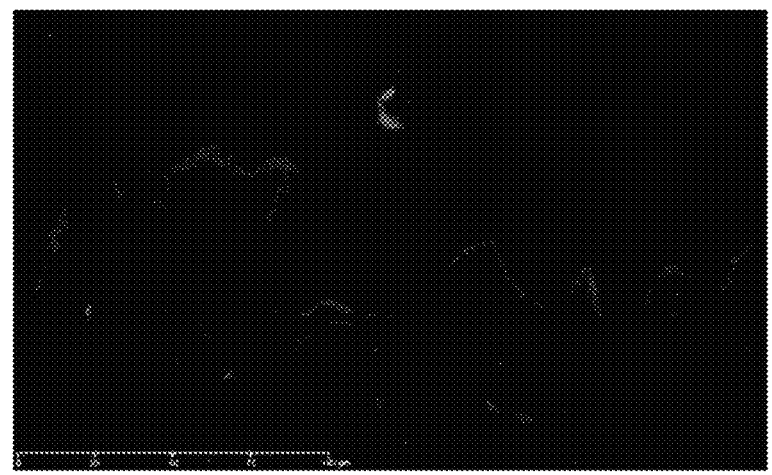
Figure 10C:
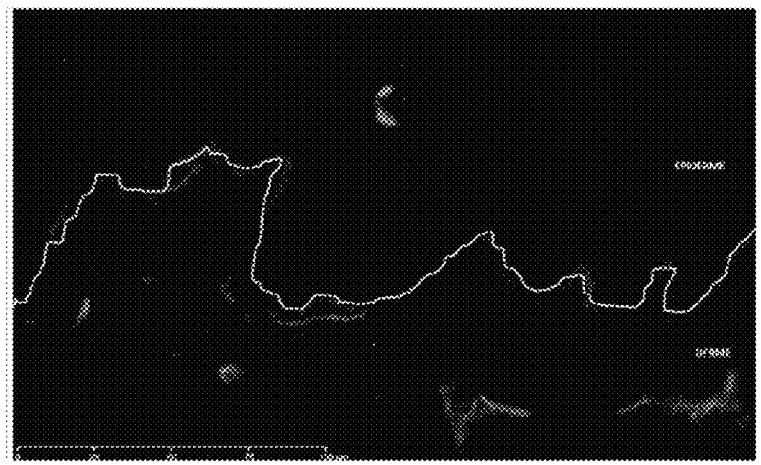

FIGS. 10A, 10B and 10C show the immunomarking of the dermis-epidermis section of skin samples of patient suffering from rosacea. FIG. 10A is stained with the anti-peripherin antibody. FIG. 10B is stained with the 3881.1 antibody. Co-marking is shown in FIG. 10C.

Figure 11A:
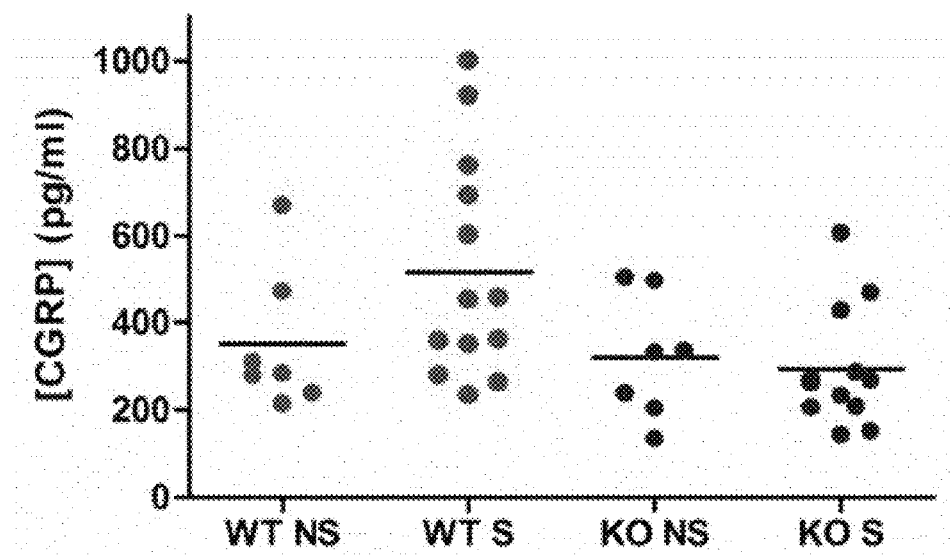
Figure 11B:
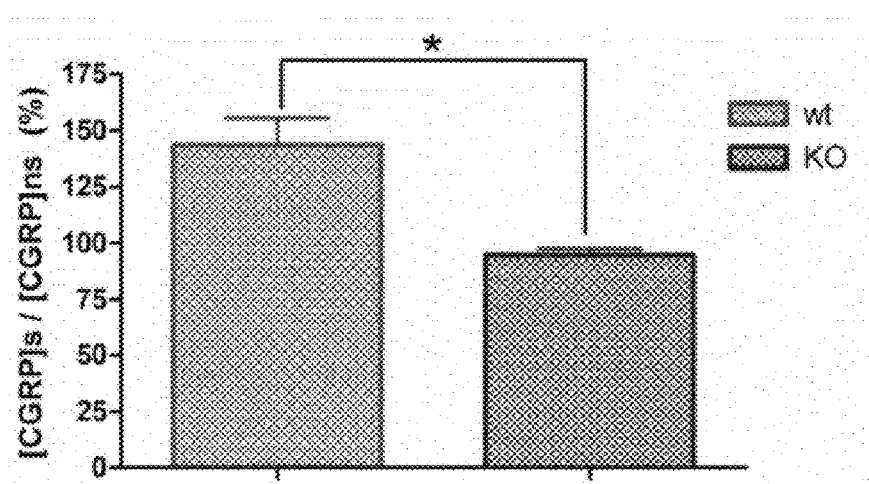

FIGS. 11A and 11B show the results of CGRP (calcitonin gene-related peptide) release experiments in primary neurone cultures, from spinal ganglia of wild mice (WT) or invalidated for the gene of Nav 1.9 (KO), after treatment (S) with capsaicin (15 min, 300 nM) or without treatment with capsaicin (NS) (see Example 3 hereafter). FIG. 11A shows the concentrations of CGRP (pg/ml) detected in the supernatant of each tested cell culture as well as the average CGRP concentrations for each group of experiments (black bar). FIG. 11B shows the ratios (in %) of the average CGRP concentration in the supernatant after stimulation, over the average concentration, before stimulation, for cell cultures from WT and KO mice, respectively. An increase of about 43.5% of the concentration of CGRP is observed after treatment with capsaicin, for cell cultures obtained from WT mice. On the other hand, no increase is observed for neurone cultures from KO cells, after stimulation with capsaicin.

DETAILED DESCRIPTION OF THE INVENTION

The Applicants prepared three polyclonal antibodies—named hereafter as Rbαa4, 3881-1 and Rbαa6—directed against human Nav 1.9. These antibodies were obtained by immunization of a non-human animal (rabbit) with an antigenic compound comprising a peptide of sequence SEQ ID No. 1, SEQ ID No. 2 or SEQ ID No. 3. The peptide of sequence SEQ ID No. 1 corresponds to a fragment of the N-terminal portion of human Nav 1.9 while the peptides of sequence SEQ ID No. 2 and SEQ ID No. 3 are fragments from intracellular loops connecting the transmembrane domains I-II and II-III of hNav 1.9, respectively. The Applicants demonstrated that these polyclonal antibodies gave the possibility of detecting in vitro the presence of Nav 1.9 and this in a specific way. It was found that these antibodies also gave the possibility of detecting the expression of Nav 1.9 at human tissues known for expressing this sodium channel, for example at dental pulp and myenteric neurones (colon). The polyclonal antibodies prepared by the Applicants prove to be reliable and sensitive biochemical tools for exploring the tissue distribution of Nav 1.9 At the end of long research work, the Applicants demonstrated, by immunomarking experiments conducted by means of the antibodies Rbαa4, 3881-1 and Rbαa6, that Nav 1.9 was locally expressed at the sensitive fibers of the skin (Example 3). Moreover, it was found that the Nav 1.9 sodium channel was more strongly expressed in skin samples from patients affected by rosacea than in skin samples from healthy individuals (Example 4). In parallel, the Applicants showed that the Nav 1.9 sodium channel was involved in releasing mechanisms of pro-inflammatory peptides by sensitive neurones, consecutively to their stimulation (Example 5). These results very strongly suggest an involvement of Nav 1.9 in the potentialization of the inflammatory response resulting from the stimulation of the sensitive fibers of skin. The Applicants therefore show for the first time that Nav 1.9 is a marker of choice for diagnosing inflammatory skin diseases, in particular rosacea.

Thus, the present invention relates to antibodies directed against human Nav 1.9, their preparation and their use in the diagnostic.

Antibodies Directed Against Nav 1.9

According to a first aspect, the invention relates to an antibody directed against human Nav 1.9 (also designated here as hNav 1.9 and Nav 1.9). By "Nav 1.9" is meant the human alpha sub-unit of the voltage-dependent sodium channels coded by the gene SCN11A, also designated as NaN, SCN12A and SNS-2 in the literature. The identification number of the human gene Nav 1.9 in the gene database of NCBI is 11289 (NCBI Gene ID). The protein sequence of human Nav 1.9 is notably described in the sequence database UniProt (sequence reference: Q9UI33) and that of NCBI (NCBI sequence reference: NP_054858). As regards the mRNA for Nav 1.9, see the NCBI reference sequence: NM_014139.

The antibody according to the invention is characterized in that it is capable of binding to an epitope included in a peptide with SEQ ID No. 1, SEQ ID No. 2 or SEQ ID No. 3.

The peptide of sequence SEQ ID No. 1 corresponds to a fragment of the N-terminal portion of hNav 1.9 (amino acids from position 31 to 47 of hNav 1.9) while the peptides of sequence SEQ ID No. 2 and SEQ ID No. 3 are fragments from intracellular loops connecting the membrane domains I-II and II-III of hNav 1.9, respectively. More specifically, the peptide of SEQ ID No. 2 corresponds to the fragment from amino acid 473 to amino acid 488 of the hNav 1.9 sequence and the peptide of SEQ ID No. 3 corresponds to the fragment from amino acid 945 to amino acid 961 of the Nav 1.9 sequence.

By "anti-Nav 1.9 antibody" or by "antibody directed against Nav 1.9" is meant any antibody or any polypeptide comprising an antibody fragment capable of recognizing and of specifically binding to an epitope of the human Nav 1.9 alpha sub-unit, preferably having an amino acid sequence included in SEQ ID No. 1, SEQ ID No. 2 or SEQ ID No. 3. Nav 1.9 may be associated with other proteins, for example with a beta sub-unit or expressed at a cell membrane or further in an isolated form (for example in a pre-purified, purified form and/or non-embedded in a cell membrane).

In a preferred embodiment, the antibody according to the invention is capable of binding to Nav 1.9 expressed at a cell membrane.

The Applicants have shown that the antibodies according to the invention are particularly suitable for use in the detection or quantification of Nav 1.9 in a biological sample, preferably a tissue sample, for example a skin sample. The antibodies according to the invention may be used for detecting or quantifying Nav 1.9 by immunomarking techniques, and/or immunoassay and/or by Western blot.

Without the intention of being bound to any theory, the Applicants are of the opinion that the detection properties of the antibodies according to the invention result from epitopes specific to Nav 1.9 against which they are directed. Indeed, the Applicants have shown that antibodies directed against other Nav 1.9 regions—for example against the peptide of SEQ ID No. 4 of the intracellular loop connecting the membrane domains II-III of Nav 1.9—either have too low sensitivity (i.e. a too small affinity for Nav 1.9) and/or a too low specificity for being used for tissue detection or quantification of Nav 1.9.

In certain embodiments, the antibody according to the invention was obtained from a preferably plasma antibody, or from a cell expressing antibodies, said antibody or cell stemming from a non-human animal immunized with an antigenic compound comprising at least one peptide having at least 90% sequence identity with SEQ ID No. 1, SEQ ID No. 2 or SEQ ID No. 3. In certain embodiments, the antigenic compound comprises at least one peptide of SEQ ID No. 1, SEQ ID No. 2 or SEQ ID No. 3 or a peptide having a sequence which differs from SEQ ID No. 1, No. 2 or No. 3 because of one, two or three amino acid modifications.

Preferably, the antigenic compound comprises a peptide of sequence SEQ ID No. 1, SEQ ID No. 2 or SEQ ID No. 3. By "antigenic compound" is meant a compound for which administration to a non-human animal, either alone or in combination with an immunoadjuvant, is capable of inducing a humoral immune reaction. In a preferred embodiment, the antigenic compound comprises several copies of said peptide, optionally coupled with each other. In certain embodiments, the antigenic compound is a carrier protein on which are grafted one or several copies of a peptide or of several peptides as defined earlier. Methods for obtaining an antibody according to the invention are described in detail hereafter.

As mentioned herein before, an antibody according to the invention may be any antibody or polypeptide comprising an antibody fragment capable of recognizing or of specifically binding to human Nav 1.9, preferably to an epitope included in an Nav 1.9 region with a sequence selected from SEQ ID No. 1, SEQ ID No. 2 and SEQ ID No. 3. The antibody according to the invention may be a monoclonal or polyclonal antibody. By "polyclonal antibodies" or "polyclonal antibody", is meant a mixture of antibodies directed against several epitopes. By "monoclonal antibody" or "monoclonal antibodies" are meant an antibody or a set of antibodies which recognize a same and single epitope.

The antibody according to the invention may be a humanized or chimeric antibody. In certain embodiments, it is prepared with a method including a step for immunization of a non-human animal. Alternatively, it may be prepared by genetic engineering techniques.

In certain embodiments, the antibody is an "integer" immunoglobulin, i.e. it has a structure of an immunoglobulin naturally present in blood plasma. This may be an immunoglobulin including 2 heavy chains and 2 light chains, for example an immunoglobulin of isotype G or a heavy chain antibody, i.e. consisting of 2 heavy chains without any light chains such as a heavy chain antibody from a camelid (HcAb) or an IgNAR from a cartilaginous fish.

In other embodiments, the antibody according to the invention is a polypeptide comprising a fragment of an immunoglobulin, preferably a variable domain capable of binding to Nav 1.9, in particular to an epitope included in a peptide of sequence SEQ ID No. 1, SEQ ID No. 2 and SEQ ID No. 3. The antibody according to the invention may be selected from a ScFv, a VH, a $V_H H$ (also called an antibody with a simple domain), a $V_{NAR}$, a Fab, or a Fab2, the chimeric and humanized versions thereof and the polypeptides comprising them. As an example, the antibody according to the invention may be a fusion protein comprising a humanized ScFv domain fused with the CH3-CH2 domains of the Fc domain of a human IgG.

In a preferred embodiment, the antibody according to the invention is a polyclonal antibody. In an additional embodiment, the antibody is specific to Nav 1.9, in particular relatively to Nav 1.5 and/or Nav 1.7. This means that the affinity of the antibody according to the invention for Nav 1.9 is greater than the one observed for another protein, in particular Nav 1.5 and/or Nav 1.7.

The specificity of the antibody according to the invention for Nav 1.9 may be determined by any method known to one skilled in the art. When the antibody according to the invention is monoclonal, for example its dissociation constant (Kd) for Nav 1.9 relatively to its possible Kd for the other protein may be compared. The dissociation constants may be determined by any suitable method, including by surface plasmon resonance. It may be considered that the antibody according to the invention is specific to Nav 1.9 relatively to another protein if its dissociation constant for Nav 1.9 is at least 10 times less, preferably at least 100 times or even at least 1,000 times less than the one observed for the other protein.

Generally, the Kd of a monoclonal antibody according to the invention is generally less than $10^{-6}$, preferably $10^{-9}$M.

When the antibody according to the invention is polyclonal, its specificity towards Nav 1.9 and to another protein by immune-marking may be evaluated as this is illustrated in the examples. For this purpose, immune-marking with the antibody according to the invention of a first cell culture expressing in a recombinant way human Nav 1.9, and of a second cell culture expressing in a recombinant way the other protein are carried out.

It is considered that the antibody is specific to Nav 1.9 relatively to the other protein if the obtained marking for the first cell culture expressing Nav 1.9 is greater (by at least 20%, preferably by at least 50% in intensity and/or in surface area) relatively to the one obtained for the second cell culture. Alternatively, the specificity of an antibody may be evaluated by Western blot experiments carried out on protein extracts from the cell systems mentioned above.

In certain embodiments, the antibody according to the invention does not bind Nav 1.5 and/or Nav 1.7. In other words, the ratio of its dissociation constant for Nav 1.9 over the one for Nav 1.5 and/or Nav 1.7 is at most equal to $10^{-3}$, preferably $10^{-4}$ and/or the marking with the antibody according to the invention of a cell culture expressing Nav 1.5 and/or Nav 1.7 (without expressing Nav 1.9) is weak, or even inexistent, as compared with the marking obtained for an identical cell line expressing Nav 1.9 (without expressing Nav 1.5 or Nav 1.7).

In other embodiments, the antibody according to the invention does not have crossed reactivity towards a protein homologous to human Nav 1.9. For example, the antibody according to the invention does not bind rat, rabbit or mouse Nav 1.9.

In an additional embodiment, the antibody according to the invention does not have cross reactivity towards hNav 1.8, and/or hNav 1.7 and/or hNav 1.5, and/or non-human Nav 1.9. In another embodiment, the antibody directed against Nav 1.9 is coupled with a means allowing its detection. The detection means may be any means known to one skilled in the art. This may be an enzyme producing a detectable signal for example by colorimetry, fluorescence, luminescence, like horseradish peroxidase, alkaline phosphatase, 3-galactosidase, or glucose-6-phosphate dehydrogenase. Alternatively, the antibody may be coupled with a chromophore, for example, a fluorescent, luminescent or colouring component. As an example of fluorescent molecules, mention may be made of Alexa or phycocyanines. The detection means may be also selected from among radionuclides such as $^{32}P$, $^{35}S$ or $^{125}I$, metal particles, for example, gold nanoparticles or further quantum dots. The detection of the antibody may also be carried out by means of a recognition system of the biotin/streptavidin or avidin type or further sugar/lectin type. In this case, the antibody may for example be coupled with biotin and detection is accomplished by means of streptavidin or avidin itself marked with a detection means such as those mentioned earlier.

In other embodiments, the antibody according to the invention is not coupled with a detection means. In this case, the antibody according to the invention may be indirectly detected by using a detection antibody (also called a secondary antibody) itself coupled with a detection means as described earlier. The detection antibody may for example be directed against the portion Fc of the antibody according to the invention.

Method for Preparing an Antibody According to the Invention

An additional object according to the invention is a method for preparing an antibody directed against human Nav 1.9. This method may comprise a step for immunization of a non-human animal with an antigenic compound comprising a peptide having at least 80% of identity, preferably at least 90% of sequence identity with SEQ ID No. 1, SEQ ID No. 2 or SEQ ID No. 3.

In certain embodiments, the method for preparing an antibody directed against Nav 1.9 comprises a step for immunization of a non-human animal with an antigenic compound comprising a peptide of SEQ ID Nos. 1, No. 2 or No. 3, or comprising a peptide for which the sequence differs from a sequence selected from among SEQ ID Nos. 1, 2 and 3 by means of two or three amino acid modifications.

In the sense of the invention, an amino acid modification encompasses the replacement (or the substitution) of an amino acid with another amino acid, the deletion of an amino acid or the insertion of an amino acid.

Preferably, the amino acid modification(s) is(are) conservative substitutions.

The non-human animal may be any animal used for generating antibodies in a laboratory or in the pharmaceutical industry. For example this may be a mouse, a rat, a goat or a rabbit. In order to obtain a heavy chain antibody, the non-human animal is selected from a camelid or a cartilaginous fish.

Preferably, the antigenic compound comprises at least one peptide, as defined herein before, preferably of sequence SEQ ID No. 1, SEQ No. 2 or SEQ ID No. 3. In certain embodiments, the antigenic compound may comprise several peptides, for example a peptide of SEQ ID No. 1 and a peptide of sequence SEQ ID No. 2, or a peptide of sequence SEQ ID No. 2 and a peptide of SEQ ID No. 3, or further a peptide of SEQ ID No. 1 and a peptide of SEQ ID No. 3.

In certain embodiments, the antigenic compound comprises a carrier protein coupled with one or several copies of said peptide or said peptides as defined herein before.

The carrier protein may for example be selected from among KLH (Keyhole Limpet Hemocyanin), a serum albumin, an ovalbumin, a poly-L-lysine or a toxoid, for example tetanus toxoid. The step for immunization of the non-human animal comprises the administration to the non-human animal of the antigenic compound, either alone or in combination with an immune-adjuvant. The immuno-adjuvant may be any immuno-adjuvant conventionally used in research, for example, Freund's adjuvant, a mineral oil like specol, squalene or an aluminium salt. The administration of the antigenic compound may be accomplished via any route, preferably via a subcutaneous, intramuscular or intra-peritoneal route. The dose of the antigenic compound varies according to the non-human animal to be immunized and is generally comprised between 10 μg and 10 mg. The administration of the antigenic compound may be renewed several times, for example 2, 3, 4, 5, 6 times until a satisfactory humoral immune response is obtained. Each administration may be spaced out in time by one or several days, typically from 7 to 30 days.

The steps of the preparation method according to the invention vary according to whether it is desired to obtain a monoclonal, polyclonal antibody or further a chimeric or humanized antibody.

The monoclonal antibodies may be obtained from cells producing antibodies, for example B lymphocytes, sampled after immunization of the non-human animal. In this case, the conventional technique for preparing hybridomas well known to one skilled in the art is used. A polyclonal antibody may be obtained from blood plasma of the non-human animal, sampled after immunization, by applying conventional purification steps like centrifugation, precipitation and affinity chromatography steps, in particular by using as an affinity ligand, a peptide derived from Nav 1.9 present in the antigenic compound used for immunizing the non-human animal or the hNav 1.9 protein itself. Affinity chromatography is preferably used in which the affinity ligand is selected from the group formed by the peptide of sequence SEQ ID No. 1, the peptide of sequence SEQ ID No. 2 and the peptide of sequence SEQ ID No. 3.

According to an additional aspect, the object of the invention is also a method for selecting an antibody directed against hNav 1.9 suitable for use for detecting or quantifying hNav 1.9 in a biological sample, preferably a tissue sample, for example a skin sample, said selection method comprising the steps of:

(a) providing one or several antibodies which may be directed against hNav 1.9, (b) putting the antibody(ies) provided in step (a) in contact with a peptide having at least 90%, preferably 100%, of sequence identity with a sequence selected from among SEQ ID No. 1, SEQ ID No. 2 and SEQ ID No. 3, said peptide being preferably immobilized on a support, and (c) selecting the antibody(ies) having formed a complex with the peptide in step (b).

The antibody(ies) of step (a) may be provided as a solution comprising a mixture of antibodies, for example a solution derived from blood plasma, in an isolated form (purified or pre-purified), each antibody being tested separately, or further as a library of antibodies expressed at the surface of phages or cells.

It is obvious that the present invention also relates to an antibody directed against Nav 1.9 obtained or which may be obtained by one of the preparation methods described above.

Uses of the Antibody According to the Invention

As mentioned earlier, the antibodies according to the invention are particularly suitable for use as a diagnostic tool for detecting and/or quantifying Nav 1.9 in biological samples. In this respect, the Applicants have shown that inflammatory skin diseases, in particular rosacea, are characterized by over-expression of Nav 1.9 at the sensitive fibers of the skin.

Thus, an additional object according to the invention is the use of an antibody according to the invention for diagnosing, prognosing and/or predicting an inflammatory skin disease.

In the sense of the invention, an "inflammatory skin pathology" or an "inflammatory skin disease" refers to a disease or a disorder affecting the skin characterized in that it is associated with, caused or may involve an inflammatory reaction. The inflammatory skin pathology may affect any portion of the skin, including the face, the scalp and the eye region, in particular the eyelids. In certain embodiments, the inflammatory reaction is a local neurogenic inflammation i.e. triggered, at least partly, by a neurologic response, in particular by the local release of pro-inflammatory neuropeptides such as the P substance and the CGRP (calcitonin gene-related peptide) peptide.

In other embodiments, the inflammatory skin disease is initiated by a neurological disorder, as this may be observed in certain cases of pruritus.

Inflammatory skin pathologies according to the invention encompass, without being limited thereto, rosacea, psoriasis, pruritus, eczema such as contact eczema and atopic dermatitis. In the sense of the invention, eczema comprises atopic eczema (also called atopic dermatitis or dermitis), contact eczema and nummular eczema. A preferred form of eczema is atopic dermatitis.

A preferred form of pruritus is a pruritus associated with an inflammatory dermatosis and/or with a skin lesion.

Rosacea comprises, without being limited thereto, erythematotelangiectatic rosacea (sub-type 1), papulopustular rosacea (sub-type 2), phymatous rosacea (sub-type 3) and ocular rosacea (sub-type 4) and granulomatous variants of rosacea.

In a preferred embodiment, the inflammatory skin pathology is erythematotelangiectatic rosacea (sub-type 1) or papulopustular rosacea (sub-type 2).

In the sense of the invention, by "diagnostic" is meant a method giving the possibility of determining whether an individual is effectively affected by an inflammatory skin pathology. By "prognosis" is meant a method giving the possibility of predicting the development of an inflammatory skin disease in a patient which is affected therewith, optionally in the presence of a therapeutic treatment. By "prediction of an inflammatory skin disease" is meant a method giving the possibility of evaluating whether an individual may develop said inflammatory skin disease.

Typically, the uses according to the invention are uses ex vivo, more exactly in vitro. In particular, these uses do not cover uses in which the antibody would be in direct interaction with the human body or an animal. The uses according to the invention generally comprise the detection or the quantification of Nav 1.9 in a biological sample of the patient by means of an antibody according to the invention. In other words, the uses according to the invention generally comprise the contacting of a biological sample from the patient under conditions allowing formation of an immune complex between Nav 1.9, potentially present in the sample, and the antibody directed against Nav 1.9, by means of which the expression of Nav 1.9 in the biological sample may be detected and/or quantified. As this will be explained hereafter, the biological sample may be subject to a certain number of treatments before its contact with the antibody directed against Nav 1.9.

The present invention also relates to a diagnostic method in vitro for an inflammatory skin disease, in an individual comprising the detection of Nav 1.9, by means of an antibody according to the invention, in a biological sample from the individual. More specifically, this method may comprise the steps:

(a) detecting or quantifying the expression of Nav 1.9 in a biological sample from the patient with an antibody according to the invention, and (b) comparing the expression of Nav 1.9 obtained in step (a) with the expression of Nav 1.9 detected or quantified in one or several biological samples from one or several control subjects.

In certain embodiments, the control subject(s) is(are) individuals suffering from the inflammatory skin disease which is desired to be diagnosed in the patient. In this embodiment, it may be considered that the patient suffers from the inflammatory skin disease if the expression of Nav 1.9 determined in step (a) is at least equal to that of the control subjects. If the expression of Nav 1.9 determined in step (a) is significantly less than the one detected for control subjects, the diagnostic is negative. Finally, if the expression of Nav 1.9 determined in step (a) is only very slightly less than the one determined for the control subjects, the patient may be diagnosed as a patient with risks, i.e. a patient which may develop the inflammatory skin disease.

In other embodiments, the control subject(s) correspond(s) to healthy patients, i.e. individuals not suffering from the inflammatory skin disease. In these embodiments, the patient is diagnosed as suffering from the inflammatory skin disease, or may suffer from it, if his/her biological sample has an expression of Nav 1.9 greater than the one of the sample(s) from healthy patients. On the other hand, if the expression of Nav 1.9 determined in step (a) is less than or equal to that of the samples from control patients (healthy), then the diagnostic may be considered as negative. It may be considered that the sample from the patient is positive if the sample has an expression for Nav 1.9 at least 10% greater, preferably at least 20% greater than that of the sample(s) of healthy patients.

The detection or quantification of Nav 1.9 in biological samples of the control subject(s) may be concomitant with those carried out for the sample from the patient or may be from data collected earlier and for example available in a database.

The object of the invention is also the use of an antibody according to the invention for evaluating the effectiveness of a drug in the treatment of an inflammatory skin disease. In order to track the effectiveness of a therapeutic treatment of an inflammatory skin disease in a patient, the following steps may be applied:
  (a) detecting or quantifying the expression of Nav 1.9, by means of the antibody according to the invention, in a biological sample of the patient before treatment,
  (b) detecting or quantifying the expression of Nav 1.9, by means of the antibody according to the invention, in a biological sample of the patient after treatment, and
  (c) comparing the expression of Nav 1.9 of step (a) with the expression of Nav 1.9 of step (b).

The effectiveness of the treatment is determined by comparing the expressions of Nav 1.9 in the samples (a) and (b). If the expression of Nav 1.9 is weaker in the sample of step (b) than in the sample of step (a), this means that the treatment is effective. If there is an increase in the expression of Nav 1.9, it may be considered that the treatment is not very active or inactive according to the significance of the observed variation. In certain embodiments, it is considered that the treatment has a therapeutic effect on the inflammatory skin disease if it involves a decrease in the expression of Nav 1.9 by at least 10%, preferably by at least 20%, still more preferably by at least 50%.

Preferably, in both steps (a) and (b), the same antibody according to the invention is used. Another object according to the invention is the use of an antibody according to the invention for tracking in vitro the development of an inflammatory skin disease. To do this, the following steps may be carried out:
  (a) detecting or quantifying the expression of Nav 1.9, by means of an antibody according to the invention, in a first biological sample of the patient at time t1,
  (b) detecting or quantifying the expression of Nav 1.9, by means of an antibody according to the invention, in a second biological sample from the patient, at a time t2 posterior to time t1, and
  (c) comparing the expression of Nav 1.9 of step (b) with the expression of Nav 1.9 of step (a).

Preferably, in both steps (a) and (b), the same antibody according to the invention is used. The comparison of the expression levels of Nav 1.9 in step (c) is a criterion giving the possibility of determining the progression or the stage of the inflammatory skin disease. It is thus possible to determine whether the disease is in regression, stationary or worsening.

If the sample of step (b) has an expression level of Nav 1.9 less than the level of expression measured in step (a), the conclusion may be drawn that rosacea is in regression. Conversely, if the sample of step (b) has an expression level of Nav 1.9 greater than the one measured in the first step, rosacea is in progression. The time t2 may be posterior by at least 1 month, preferably by at least 6 months, or even by at least 1 year at time t1.

The object of the invention is also the use of an antibody according to the invention for generating data and/or useful information for diagnosing, and/or for predicting and/or for tracking the development of an inflammatory skin disease, these methods may contain any of the combinations of steps described above.

In the whole of the methods and uses described above, the inflammatory skin disease may be selected from a rosacea, psoriasis, pruritus, contact eczema and atopic dermatitis. Preferably, this is rosacea, for example the rosacea of sub-type 1 (erythematotelangiectatic rosacea), the rosacea of sub-type 2 (papulopustular rosacea), rosacea or a granulomatous variant of rosacea.

In the whole of the uses and methods described above, the biological sample(s) is(are) preferably skin samples. This may be a sample of dermis or of dermis-epidermis or further of epidermis. Preferably, this is a skin sample comprising sensitive nerve fibers. As an example, this may be a skin biopsy of variable size typically from 0.1 to 1 mm in diameter. As this is detailed hereafter, the biological sample may be subject to one or several treatments in order to allow detection or quantification of Nav 1.9 by an antibody according to the invention.

The methods and uses according to the invention are based on a step for putting the biological sample into contact with the antibody according to the invention under conditions allowing the formation of an immune complex between Nav 1.9, potentially present in the sample, and said antibody. The detection and/or the quantification of Nav 1.9 in the sample is generally achieved via the formation and optionally the detection of the immune complex.

The detection and/or quantification of Nav 1.9 by means of an antibody according to the invention may be achieved by any method known to one skilled in the art, for example by immunoassay, by Western blot or by immuno-marking, in particular by immunohistochemistry or by immunocytochemistry. As examples of immunoassay techniques, mention may be made of radio-immunological assays (RIA), magnetic immunoassays (MIA), sandwich or competitive ELISA tests. The quantification and/or the detection of Nav 1.9 in a biological sample may be based on a separative step by immuno-chromatography in which the antibody according to the invention is used as an affinity ligand. Detecting or quantifying Nav 1.9 may be contemplated in a biological sample by immunoprecipitation or further by surface plasmon resonance in which the antibody according to the invention is immobilized at the surface of the sensor.

The preferred techniques are immunohistochemistry and Western blot. These are well known techniques to one skilled in the art. Examples of applications are shown in the experimental part of the present application.

Briefly, the technique by Western blot comprises the preparation of a protein extract from the biological sample, the application of an electrophoresis step generally under denaturating conditions (SDS-PAGE gel), the transfer of proteins having migrated on a membrane and then a step for immunodetection by means of a primary antibody (anti-Nav 1.9 antibody according to the invention) and then a step for revealing the possibly formed antibody-Nav 1.9 complex.

For detection or quantification of Nav 1.9 in a biological sample by Western blot, it is preferred to use an antibody according to the invention directed against an epitope included in a peptide of sequence SEQ ID No. 1 or SEQ ID No. 3.

The immunohistochemistry technique comprises the preparation of a tissue section, preferably of the dermis, which may either be cryofixed, or chemically fixed. The tissue section may then be included in a resin and/or rehydrated and then incubated with the antibody according to the invention under conditions favorable for the formation of the antibody-Nav 1.9 complex. The detection of the complex may be carried out directly if the antibody is coupled with a detection means or, if necessary by means of a secondary antibody. Generally, the detection means coupled with the antibody according to the invention, or if necessary with the secondary antibody is a fluorescent molecule. The detection of the Nav 1.9-antibody complexes according to the invention may then be carried out by fluorescence microscopy. In certain embodiments, in order to view the cell structures at the level of which is expected an expression of Nav 1.9, co-marking with a second antibody may be carried out. As an example, in order to view the sensitive nerve fibers of the dermis, co-marking with an anti-peripherin antibody may be carried out. In a preferred embodiment, in order to detect or quantify Nav 1.9 in a skin sample by immune-marking, an antibody directed against an epitope included in a peptide of sequence SEQ ID No. 2 is used. The skin sample is preferably a cryofixed dermis section.

In certain embodiments, the methods uses according to the invention may comprise the detection of an additional marker to Nav 1.9 or the evaluation of a particular symptom of the inflammatory skin disease. As an example, when the inflammatory skin disease is rosacea, the methods according to the invention may comprise the detection of an additional marker or of a symptom of rosacea such as papules, vascular hyperreactivity, erythema, or sensations of burns, itching or cuts.

Finally, the invention also relates to a kit, or to the use of said kit, for the diagnostic of an inflammatory skin disease. The kit comprises an antibody according to the invention and optionally a means for detecting said antibody. The diagnostic kit may also comprise one or several additional objects, for example, an explanatory sheet for applying the diagnostic test, one or several reagents for preparing the biological sample, or further one or several means useful for sampling the biological sample.

The inflammatory skin pathology may be selected from rosacea, psoriasis, pruritus, contact eczema and atopic dermatitis. Preferably, this is rosacea, for example the rosacea of sub-type 1 (erythematotelangiectatic rosacea), the rosacea of sub-type 2 (papulopustular rosacea), or a granulomatous variant of rosacea.

Other aspects and advantages of the present invention will become apparent upon reading the examples which follow. These examples should be considered as illustrative and by no means as limiting the scope of the invention.

EXAMPLES

Example 1: Preparation of Polyclonal Antibodies

Antibodies Rbαa4 and Rbαa6:

Two rabbits were each immunized with a peptide mixture containing the 2 peptides (SEQ ID No. 1 and SEQ ID No. 3) coupled with KLH (calendar hereafter).
Control of the immune response with ELISA. Purification on an affinity column (Hi-trap NHS coupling) of the samples D63 and D77.

The antibody Rbαa4 was isolated by a purification method comprising an affinity chromatography step in which the immobilized ligand was the peptide of SEQ ID No. 1.

The antibody Rbαa6 was isolated by a purification method comprising an affinity chromatography step in which the immobilized ligand was the peptide of SEQ ID No. 3.

Antibodies 3881.2 and 3881.1:

Two rabbits were each immunized with a peptide mixture containing the 2 peptides (SEQ ID No. 2 and SEQ ID No. 4) coupled with KLH (calendar hereafter). Purification on an affinity column (AF—Amino TOYOPEARL/MBS) of the samples D28. The antibody 3881.1 was isolated by a purification method comprising an affinity chromatography step in which the immobilized ligand was the peptide of SEQ ID No. 2. The antibody 3881.2 was isolated by a purification method comprising an affinity chromatography step in which the immobilized ligand was the peptide of SEQ ID No. 4.

| Antibody reference | Antigenic peptide | Number of immunizations | Sampling/purification day |
|---|---|---|---|
| Rbαa4 | N-terminal of Nav 1.9 (SEQ ID No. 1) | 5 (D0, D14, D28, D42, D56) | D63-D77 |
| 3881.1 | Peptide of the intracellular loop I-II (SEQ ID No. 2) | 4 (D0, D7, D10, D18) | D28 |
| 3881.2 | Peptide of the intracellular loop II-III (SEQ ID No. 4) | 4 (D0, D7, D10, D18) | D28 |
| Rbαa6 | Peptide of the intracellular loop II-III (SEQ ID No. 3) | 5 (D0, D14, D28, D42, D56) | D63-D77 |

Example 2: Characterizations of the Antibodies

1. Immunofluorescence on Heterologous Systems

A heterologous expression system was used for selecting the antibodies and testing their specificity. HEK-293 cells were transfected: 1) with a plasmid containing the nucleic sequence coding for the human Nav 1.9 alpha sub-unit labelled myc at its C-terminal end or 2) with the sequences coding for human Nav 1.5 or Nav 1.7 (hNav 1.5 and hNav 1.7). As the latter were not labeled, they were co-transfected with a plasmid coding for expression of GFP.

24 h after transfection, the cells were fixed with 2% paraformaldehyde (PAF), permeabilized with 0.1% Triton and then incubated with the anti-hNav 1.9 antibody to be tested. The expression of hNav 1.9 is tested by co-marking with an anti-myc monoclonal antibody while the expression of hNav 1.5 and hNav 1.7 is tested with a PanNav antibody recognizing all the sodium channels.

—Results

The marking of the heterologous system expressing hNav 1.9-myc with the Rbαa4 antibody or Rbαa6 antibody is co-localized with the anti-myc marking. No marking by Rbαa4 and by Rbαa6 of the non-transfected cells is distinguished, which shows that these antibodies do not bind to an endogenous protein. As an illustration, FIGS. 1A and 1B show the co-marking results with the anti-myc monoclonal antibody and the polyclonal Rbαa4 antibody for recombinant cells expressing hNav 1.9-myc (FIG. 1A) and non-recombinant cells (FIG. 1B). Identical markings were obtained for the Rbαa6 antibody (data not shown).

It also appears that the Rbαa4 and Rbαa6 antibodies do not mark the heterologous systems expressing hNav 1.5 and hNav 1.7, for which the identity percentage is 56% and 55% with hNav 1.9. This shows that Rbαa4 and Rbαa6 do not have any crossed reactivity towards hNav 1.5 and hNav 1.7. In this respect, FIGS. 2A and 2B show the immuno-marking results with the Rbαa4 antibody of the HEK cells expressing hNav 1.5, identified by GFP (FIG. 2A) and of HEK cells expressing hNav 1.7, identified by GFP (FIG. 2B). While the signal emitted by GFP is clearly visible, the marking with Rbαa4 of the cells is very weak or even inexistent.

The marking with an anti-PanNav monoclonal antibody confirmed the proper expression of hNav 1.5 or hNav 1.7 by HEK cells. Identical markings were obtained for the Rbαa6 antibody (data not shown). The Rbαa4 and Rbαa6 antibodies therefore specifically recognize hNav 1.9 and do not have any cross reactivity with hNav 1.5 and hNav 1.7.

No marking is detected with the antibody 3881.2 directed against the peptide of SEQ ID No. 4 at all with transfected or non-transfected cells. This lack of detection results from the chemical fixing method which should induce alteration of the conformation of the region of hNav 1.9 recognized by this antibody. On the other hand, this antibody very effectively and sensitively marks tissues not chemically fixed, expressing endogenously Nav 1.9 (see hereafter).

The antibody directed against the peptide of SEQ ID No. 4 is incapable of detecting hNav 1.9, regardless of the cell system and the analyzed tissue.

2. Western Blot

Analyses by Western blot of protein extracts from lysis of HEK cells transfected with hNav 1.9-myc were carried out in order to confirm the specificity of detection of the Rbαa4 and Rbαa6 antibodies.

—Results

The Rbαa4 and Rbαa6 antibodies recognize a band having a molecular weight around 250 kDa (FIG. 3). This band is also present during the detection with the anti-myc antibody. Further, this band is not detected for the extract from non-transfected cells (negative control).

The molecular weight of the specific band is slightly greater than the expected molecular weight for hNav 1.9-Myc (about 210 kDa). This molecular weight difference is certainly ascribable to post-translational modifications, in particular to glycosylations. A deglycosylation experiment on the protein lyzate was conducted and demonstrated a decrease in the intensity of the 250 kDa band, which confirms this assumption.

3. Immunohistochemistry on Human Tissues

Tests for immune-marking myenteric ganglions, of human dental pulp and of trigeminal ganglia were conducted by means of the Rbαa4, Rbαa6 and 3881.1 antibodies. The samples were prepared in the following way:

Myenteric ganglia: Colon operative residues are rapidly recovered after sampling, placed on ice in carbogen-gassed Krebs solution, added with muscular contraction blockers (atropin, 2 μM and nicardipin, 6 μM), before dissection.

Composition of the carbogen-gassed Krebs solution (in mM): 118 NaCl, 4.8 KCl, 1 NaH$_2$PO$_4$, 25 NaHCO$_3$, 1.2 MgCl$_2$, 2.5 CaCl$_2$ and 11 glucose, at equilibrium at pH 7.4 with 95% O$_2$-5% CO$_2$.

The dissection consists of removing the mucosa, the sub-mucosa and of reducing the thickness of the tissue by removing a little muscle (longitudinal and circular muscle) (Osorio and Delmas, 2010, Nature Protocols, 6(1):15-27).

The tissue is then incubated for 1 h in PBS 4% sucrose (mass/volume) at 4° C., and then for 12 h in PBS 20% sucrose, always at 4° C.

Composition of the PBS (in mM): 140 NaCl, 10 mM of PO$_4$ Buffer (NaHPO$_4$ and NaH$_2$PO$_4$), 3 mM KCl, pH 7.2.

Dental pulp: After sampling, the wisdom tooth is kept in PBS at 4° C. The dental pulp is extracted from the enamel, and then incubated for 1 h in PBS 4% sucrose (mass/volume) at 4° C., and then for 12 h in PBS 20% sucrose, always at 4° C.

Trigeminal ganglion: After sampling (12-24 h post-mortem), the ganglia are incubated for 2 h in PBS 4% sucrose (mass/volume) at 4° C., and then for 12 h in PBS 20% sucrose, always at 4° C.

Finally, the tissues are included in OCT and frozen in isopentane cooled with dry ice. The blocks are stored at −80° C.

The transverse sections of 15-30 μm are made at the cryostat, mounted on Superfrost slides, dried (1 h under Sorbonne) and then stored at −80° C. until use.

Upon leaving the freezer, the slides are dried for 30 min under a Sorbonne.

The tissues may then be treated in two different ways depending on whether the primary antibody requires a "fresh" or "fixed" tissue. They are therefore:

Rehydrated with PBS for 1 h: "cryofixed tissue"

or fixed with paraformaldehyde (PAF) at 4% (volume/volume) for 10 min, and then rinsed 4×10 min in PBS: "chemically fixed tissue"

Immuno-Marking Procedure

The sections are incubated for 1 h30 at room temperature in a saturation medium: PBS+3% (mass/volume) of BSA+ 0.3% (volume/volume) of Triton X-100. The primary antibodies are added to the saturation medium for 12 h incubation at 4° C. in a humid chamber. The sections are then rinsed 4 times for 15 min in PBS before 45 min of incubation at room temperature with the secondary antibodies in PBS+ 3% (mass/volume) of BSA in a humid chamber. Finally, the sections are rinsed 4 times for 15 min in PBS before being mounted in a mounting medium (Mowiol or Prolong Gold)

Co-marking with an anti-HuC/D or anti-NF200 antibody for the myenteric ganglia, with an anti-peripherin antibody for the dental pulp and with an anti-NF200 antibody was carried out in order to view the neurones and the nerve fibers.

Results

The Rbαa4 and Rbαa6 antibodies give an interesting marking for the various human tissues, regardless of whether they are chemically or cryo-fixed (data not shown). The antibody 3881.1 efficiently and sensitivity marks the cryo-fixed tissues, in particular of dental pulp and of the myenteric plexus, known for expressing Nav 1.9. On the other hand, it is inefficient on chemically fixed tissue (data not shown).

These immune-marking experiments therefore confirmed the possibility of using the antibodies Rbαa4, Rbαa6 and 3881.1 as a tool for exploring tissue expression of hNav 1.9.

Example 3: Expression of hNav 1.9 by Skin Sensitive Nerve Fibers

Detection of the expression of Nav 1.9 at the skin nerve fibers was explored by marking with immunofluorescence by means of polyclonal antibodies directed against the alpha sub-unit of the human Nav 1.9 voltage-dependent sodium channel, i.e. the antibodies Rbαa6, Rbαa4 and the antibody 3881.1.

Co-marking by means of an antibody directed against peripherin, a specific protein of the peripheral nervous tissue, was carried out in order to localize the nerve fibers.

Various types of skin samples were used: deep dermis, dermis, dermis-epidermis interface and hair follicle.

—Preparation of the Samples

The skin samples were prepared in the following way:

After disinfecting the skin, 3 mm skin biopsies were carried out in a patient subject to local anesthesia at the site of the biopsy. The biopsy is washed in PBS pH7.2 and placed in an Eppendorf tube in liquid nitrogen. The Eppendorf is then stored at −80° C. until inclusion in an OCT matrix. Frozen sections with a thickness of 10 µm were then made.

—Procedure for Marking by Immunofluorescence

The sections are incubated for 1 h30 at room temperature in a saturation medium: PBS+3% (mass/volume) of BSA+ 0.3% (volume/volume) of Triton X-100. The primary antibodies are added to the saturation medium for 12 h incubation at 4° C. in a humid chamber. The sections are then rinsed 4 times for 15 min in PBS before 45 min of incubation at room temperature with the secondary antibodies in PBS+ 3% (mass/volume) of BSA in a humid chamber. Finally, the sections are rinsed 4 times for 15 min in PBS before being mounted in a mounting medium (Mowiol or Prolong Gold).

—Results

FIGS. 4A and 4B and 5A, 5B, and 5C show the marking by immunofluorescence of deep dermis sections with the anti-peripherin antibody (FIGS. 4A and 5A), the antibody Rbαa6 (FIG. 4B), and the antibody 3881.1 (FIG. 5B). The immune-marking results obtained with the antibodies Rbαa6 and 3881.1 are similar. Similar immune-marking results of the dermis were obtained with the Rbαa4 antibody (data not shown). An expression of the Nav 1.9 sodium channel localized at the sensitive fibers of the deep dermis is observed. Sharp co-localization areas of the peripherin and of Nav 1.9 are revealed in FIGS. 4C and 5C.

FIGS. 6A, 6B 6C, 7A, 7B and 7C show the immunomarking results of the peripherin and of Nav 1.9 at the dermis-epidermis interface and of a hair follicle respectively. These immuno-marking photographs were obtained with the antibody 3881.1.

FIGS. 6A, 6B and 6C shows the localized expression of Nav 1.9 at an isolated nerve fiber of the dermis. A similar result is observed at the hair follicle where Nav 1.9 is expressed, in a localized way, by the sensitive fibers innervating the follicle (FIGS. 7A, 7B and 7C). No marking was detected in the dermis.

—Conclusions

These immuno-marking experiments show that the Nav 1.9 sodium channel is expressed at the skin sensitive fibers, both in the epidermis and in the deep dermis. The antibodies according to the invention prove to be tools of choice for detecting and quantifying Nav 1.9 in skin samples.

Example 4: Over-Expression of Nav 1.9 by Skin Sensitive Fibers in Patients Affected with Rosacea Preparation of the Samples The skin samples (dermis and hair follicle) were prepared as described in Example 1: After disinfecting the skin, 3 mm skin biopsies were made in a patient affected with rosacea and subject to local anesthesia at the site of the biopsy. The biopsy is washed in PBS pH7.2 and placed in an Eppendorf tube in liquid nitrogen. The Eppendorf is then stored at −80° C. until inclusion in an OCT matrix. Frozen sections with a thickness of 10 µm were then made.

—Marking Procedure by Immunofluorescence

The immune-marking procedure is similar to the one described for Example 1.

The following antibodies were used:

For the peripherin, the primary antibody is a monoclonal antibody (Millipore, MAB1527) of mice and the secondary antibody is a donkey anti-mouse antibody coupled with Alexa488 (Invitrogen, A-21202).

For Nav 1.9, the primary antibody is the rabbit polyclonal antibody 3881.1 and the secondary antibody is a donkey anti-rabbit antibody coupled with TRITC (Jackson Immunoresearch).

—Results

FIGS. 8A, 8B, 8C, 9A, 9B, 9C 10A, 10B and 10C show the immuno-marking results of the peripherin and of Nav 1.9 at the dermis, at a hair follicle and at the dermis/epidermis interface from skin samples affected by rosacea. Nav 1.9 is localized at the sensitive fibers of the dermis and of the hair follicle. While a relatively homogenous marking was observed for healthy skin samples, the presence of expression clusters i.e. localized areas (spots) having a very high expression of Nav 1.9 is observed. FIGS. 10A, 10B and 10C moreover shows an expression of Nav 1.9 in the epidermis, which had not been observed for healthy samples.

These preliminary results therefore show over-expression of Nav 1.9 at skin samples affected by rosacea.

Example 5: Demonstrating the Involvement of the Nav 1.9 Sodium Channel in the Neuro-Inflammatory Response The goal of this study was to demonstrate the impact of Nav 1.9 on the release of the calcitonin gene-related peptide (CGRP). The CGRP peptide is a powerful vasodilator and a pain mediator at the peripheral and central nervous system. CGRP is also involved in peripheral neurogenic inflammation, in particular of skin. For this purpose, the Applicants compare the release of CGRP by primary cultures of neurones, after or without treatment with capsaicin. The primary neurone cultures were obtained from spinal ganglia (dorsal root ganglion—DRG) taken from wild mice (WT) and from mice in which the gene of the Nav 1.9 sodium channel was invalidated (KO mice for Nav 1.9).

—Primary Cultures of Neurones from Spinal Ganglia of Adult Mice.

The samples of spinal ganglia were made in C57BL6 male mice from 2 to 3 months old. On average, 20 spinal ganglia were taken per mouse, which corresponds to a total of 50,000 and 80,000 neurones/mouse.

The collected neurones were sown in 96-well plates in an amount of 10,000 cells per well. The wells were covered beforehand with poly-L-Lysine (12 ng/cm$^2$) and laminin (6 ng/cm$^2$) in order to promote adhesion of the neurones. The cells were incubated for 24 h at 37° C. before beginning the test, in a suitable culture medium (D-MEM supplemented with glucose, NEAA,L-glutamine, pyruvate, NGF (Nerve Growth Factor 2.5 s mouse submaxillary) GDNF (Glial cell-line Derived Neurotrophic Factor) and fetal calf serum).

All in all, the cell cultures were obtained from 12 mice (6 WT and 6 KO). 5 to 8 neurone primary culture wells were prepared per mouse.

—Quantification of the Release of CRGP in the Medium after Treatment with Capsaicin A portion of the primary cultures (3 to 5 culture wells per mouse) were incubated for 15 min in the presence of capsaicin at 300 nM. The second portion of the primary cultures (2 to 3 culture wells per mouse) were not subject to any treatment.

The dosage of released CGRP in the supernatant was achieved by ELISA assay by using the kit SPIbio ref.

A05482 intended for dosage of rat CGRP, but which may also be used for quantifying mouse CRGP.

Briefly, the supernatants of the primary cultures were sampled and diluted to ⅕ before being added into the wells of a microplate covered with an anti-CGRP monoclonal antibody. A second anti-CGRP antibody (polyclonal), coupled with acetylcholine esterase, was then added. After incubation and rinsing, detection was achieved by means of Ellman's reagent (DTNB) by measuring absorbance at 405 or 414 nm.

—Results

The results are illustrated by FIGS. 11A and 11B.

In the primary cultures obtained from wild mice (WT), it is observed that the treatment with capsaicin caused a significant increase in the amount of CGRP (+43.5%) present in the supernatant. On the other hand, no variation in the amount of CGRP released in the supernatant was observed for the primary cells from KO mice: the amount of CGRP detected in the supernatant is equivalent to the basal level, before stimulation with capsaicin, of CGRP of the supernatant of the WT cells.

Nav 1.9 is therefore involved in the regulation of the release of CGRP consecutively to stimulation with capsaicin.

Example 6: Quantification of the Intracellular Pool of CGRP in Neurone Cultures Obtained from Wild Mice (WT) and KO Mice for Nav 1.9 (KO)

—Primary Cultures of Neurones from Spinal Ganglia of Adult Mice.

The procedure used is identical with that of Example 3. The primary neurone cultures were prepared from 4 KO mice and 4 WT.

—Dosage of the Intracellular Pool of CGRP.

After incubation for 24 h at 37° C. and rinsing, the primary cultures were lyzed with Triton X100 at 1%. The dosage of the CGRP peptide in cell lyzates was carried out with the Elisa test described in Example 3.

It is found that the average concentration of CRPG for the primary cultures from KO mice is slightly less than the one obtained for primary cultures from wild mice. Nevertheless, the observed difference is not significant.

Accordingly, the difference in releasing of CGRP, under stimulation with capsaicin, observed for the WT and KO primary neurone cultures, in Example 3, cannot be ascribed to intracellular deficiency in CGRP in the KO primary neurone cells.

CONCLUSION

The results of release of the CGRP peptide by primary neurone cultures, from WT and KO mice, after or without stimulation with capsaicin, and the immunomarking results of dermis and epidermis sections very strongly suggests the involvement of Nav 1.9 in the potentialization of the neurogenic inflammation observed at the skin in inflammatory skin pathologies. Nav 1.9 therefore is a marker of interest for the diagnostic of inflammatory skin diseases, in particular rosacea.

| Table of sequences | |
|---|---|
| Reference | Sequence |
| SEQ ID No. 1 | Peptide included in the N-terminal end of hNav 1.9: IAIQKEKKKSKDQTGEV |
| SEQ ID No. 2 | Peptide of the intracellular loop I-II ESGKDQPPGSDSDEDC |
| SEQ ID No. 3 | Peptide of the intracellular loop II-III QAYELHQENKKPTSQRV |
| SEQ ID No. 4 | Peptide of the intracellular loop II-III SNEERNGNLEGEARK |

The invention claimed is:

1. An antibody directed against human Nav 1.9, wherein the antibody binds to an epitope formed by one or more amino acid sequences selected from the group consisting of SEQ ID No. 1 ("SEQ1"), SEQ ID No. 2 ("SEQ2"), SEQ ID No. 3 ("SEQ3"), a sequence at least 90% identical to SEQ1, a sequence at least 90% identical to SEQ2, a sequence at least 90% identical to SEQ3, a sequence that differs from SEQ1 by one amino acid, a sequence that differs from SEQ1 by two amino acids, a sequence that differs from SEQ1 by three amino acids, a sequence that differs from SEQ2 by one amino acid, a sequence that differs from SEQ2 by two amino acids, a sequence that differs from SEQ 2 by three amino acids, a sequence that differs from SEQ3 by one amino acid, a sequence that differs from SEQ3 by two amino acids, and a sequence that differs from SEQ3 by three amino acids.

2. The antibody of claim 1, wherein the antibody is suitable for detecting or quantifying Nav 1.9 in a biological sample.

3. The antibody of claim 1, wherein the antibody is a polyclonal antibody.

4. The antibody of claim 1, wherein the antibody is selected from the group consisting of a monoclonal antibody, an antibody with a single domain ("sdab"), an immunoglobulin new antigen receptor ("IgNar") and a polypeptide comprising a variable domain of an antibody.

5. The antibody of claim 1, wherein the antibody does not bind to Nav 1.5 and Nav 1.7.

6. The antibody of claim 1, wherein the antibody is obtained from a pool of antibodies, blood plasma, or cells expressing antibodies.

7. The antibody of claim 1, wherein the antibody is coupled with a detection means.

8. The antibody of claim 6, wherein the antibody is obtained from a non-human animal immunized with an antigenic compound comprising one or more amino acid sequence(s) selected from the group of claim 1.

9. The antibody of claim 2, wherein the biological sample is a skin sample.

10. The antibody of claim 4, wherein the monoclonal antibody is an immunoglobulin ("Ig").

11. The antibody of claim 4, wherein when the antibody comprises of a variable domain of an antibody, the variable domain being selected from the group consisting of ScFv, VH, $V_HH$, $V_{NAR}$, and Fab and chimeric and humanized versions thereof.

12. The antibody of claim 7, wherein the detection means comprises a detectable signal.

13. The antibody of claim 12, wherein the detectable signal is a signal comprising one or more chromophore, fluorescent compound, luminescent compound, radionuclide, metal particle, biotin, streptavidin, avidin, sugar and lectin.

14. The antibody of claim 12, wherein the signal is produced in association with an enzyme.

15. The antibody of claim 14, wherein the enzyme comprises of one or more horseradish peroxidase, alkaline phosphatase, 3-galactosidase, and glucose-6-phosphate dehydrogenase.

16. The antibody of claim 13, wherein the radionuclide comprises of one or more $^{32}P$, $^{35}S$ and $^{125}I$.

17. The antibody of claim 13, wherein the metal particle comprises of one or more gold nanoparticle.

18. A kit for diagnosing an inflammatory skin disease, the kit comprising one or more antibody of claim 1, wherein the kit optionally comprises a means for detecting said antibody.

19. A method for preparing an antibody directed against human Nav 1.9, the method comprising immunizing a non-human animal with an antigenic compound comprising at least one peptide of SEQ ID No. 1, SEQ ID No. 2 or SEQ ID No. 3 or a peptide having a sequence which differs from SEQ ID No. 1, No. 2 or No. 3 because of one, two or three amino acid modifications.

20. The method according to claim 19, wherein the antigenic compound comprises a carrier protein coupled with one or several copies of said peptide.

21. The method according to claim 19, further comprising recovering the antibody directed against human Nav 1.9 from the blood plasma of the non-human animal, after immunization.

22. The method according to claim 19, wherein the antibody directed against human Nav 1.9 is produced by a hybridoma obtained from a cell expressing antibodies.

23. The method according to claim 22, wherein the cell expressing antibodies is a B lymphocyte from the non-human animal after immunization.

* * * * *

SEQUENCE LISTING

```
<160> NUMBER OF SEQ ID NOS: 4

<210> SEQ ID NO 1
<211> LENGTH: 17
<212> TYPE: PRT
<213> ORGANISM: Artificial Sequence
<220> FEATURE:
<223> OTHER INFORMATION: Fragment de hNav1.9

<400> SEQUENCE: 1

Ile Ala Ile Gln Lys Glu Lys Lys Lys Ser Lys Asp Gln Thr Gly Glu
1               5                   10                  15

Val

<210> SEQ ID NO 2
<211> LENGTH: 16
<212> TYPE: PRT
<213> ORGANISM: Artificial Sequence
<220> FEATURE:
<223> OTHER INFORMATION: Fragment de hNav1.9

<400> SEQUENCE: 2
```

-continued

```
Glu Ser Gly Lys Asp Gln Pro Pro Gly Ser Asp Ser Asp Glu Asp Cys
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Fragment de hNav1.9

<400> SEQUENCE: 3

Gln Ala Tyr Glu Leu His Gln Glu Asn Lys Lys Pro Thr Ser Gln Arg
1               5                   10                  15

Val

<210> SEQ ID NO 4
<211> LENGTH: 15
<212> TYPE: PRT
<213> ORGANISM: Artificial Sequence
<220> FEATURE:
<223> OTHER INFORMATION: Fragment de hNav1.9

<400> SEQUENCE: 4

Ser Asn Glu Glu Arg Asn Gly Asn Leu Glu Gly Glu Ala Arg Lys
1               5                   10                  15
```